United States Patent [19]

Tuneberg et al.

[11] Patent Number: 5,697,780
[45] Date of Patent: Dec. 16, 1997

[54] ORTHODONTIC APPLIANCE KIT AND COMPONENTS

[75] Inventors: Lee H. Tuneberg; John E. Viglieltti, both of Sheboygan, Wis.

[73] Assignee: American Orthodontics Corporation, Sheboygan, Wis.

[21] Appl. No.: 580,601

[22] Filed: Dec. 29, 1995

Related U.S. Application Data

[60] Provisional application No. 60/005,442, Oct. 12, 1995.

[51] Int. Cl.⁶ ................................................. A61C 7/12
[52] U.S. Cl. ..................................... 433/9; 206/369
[58] Field of Search .......................... 433/8, 9, 29, 229, 433/136, 43; 206/369, 776, 778, 460; 4/595, 638

[56] References Cited

U.S. PATENT DOCUMENTS

| | | | |
|---|---|---|---|
| 3,361,252 | 1/1968 | Wise | 206/460 |
| 3,709,866 | 1/1973 | Waller | 260/27 R |
| 3,745,653 | 7/1973 | Cohl | 433/9 |
| 3,854,581 | 12/1974 | Jones, Jr. | 206/460 |
| 4,204,325 | 5/1980 | Kaelble | 433/9 |
| 4,701,129 | 10/1987 | Hazard | 433/136 |
| 4,801,528 | 1/1989 | Bennett | 433/220 |
| 4,859,184 | 8/1989 | Hazard | 433/136 |
| 4,978,007 | 12/1990 | Jacobs et al. | 206/469 |
| 5,172,809 | 12/1992 | Jacobs et al. | 206/368 |
| 5,172,810 | 12/1992 | Brewer | 206/369 |
| 5,183,403 | 2/1993 | Masuhara et al. | 433/9 |
| 5,279,800 | 1/1994 | Berry, Jr. | 206/369 |
| 5,348,154 | 9/1994 | Jacobs et al. | 206/369 |
| 5,368,161 | 11/1994 | Plais | 206/369 |
| 5,484,283 | 1/1996 | Franetzki | 433/29 |
| 5,542,844 | 8/1996 | Perret, Jr. | 433/9 |

*Primary Examiner*—Cary E. O'Connor
*Attorney, Agent, or Firm*—Lloyd L. Zickert

[57] ABSTRACT

Apparatus and method for prepasting orthodontic appliances such as brackets with a light-cure adhesive and facilitating the mounting of the brackets in the mouth of a patient. The apparatus includes a kit having a storage box capable of storing a plurality of bond cards on which prepasted brackets are mounted in an organized fashion, a work box for facilitating the initial mounting of the brackets on the bond cards, a bond card cover for protecting the prepasted brackets against curing of the adhesive at the chairside of the patient, and a mouth shield for delaying the curing of the adhesive following initial placement of the prepasted brackets in the mouth of a patient.

21 Claims, 4 Drawing Sheets

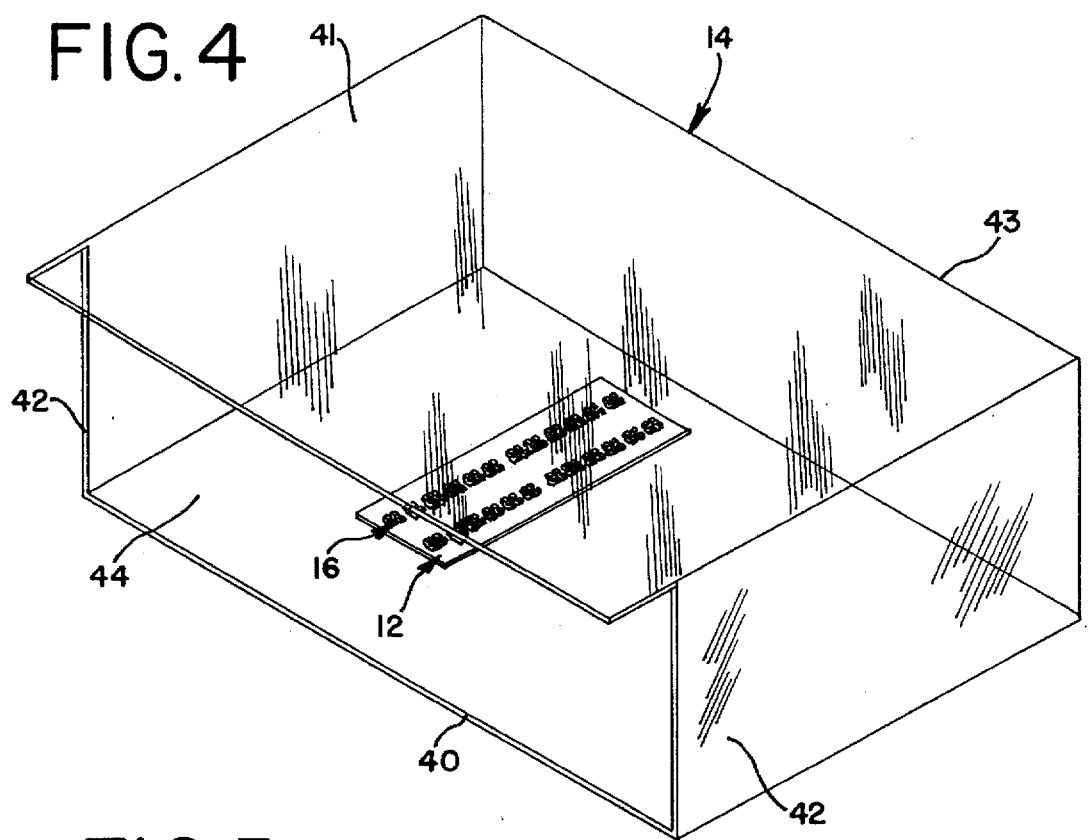
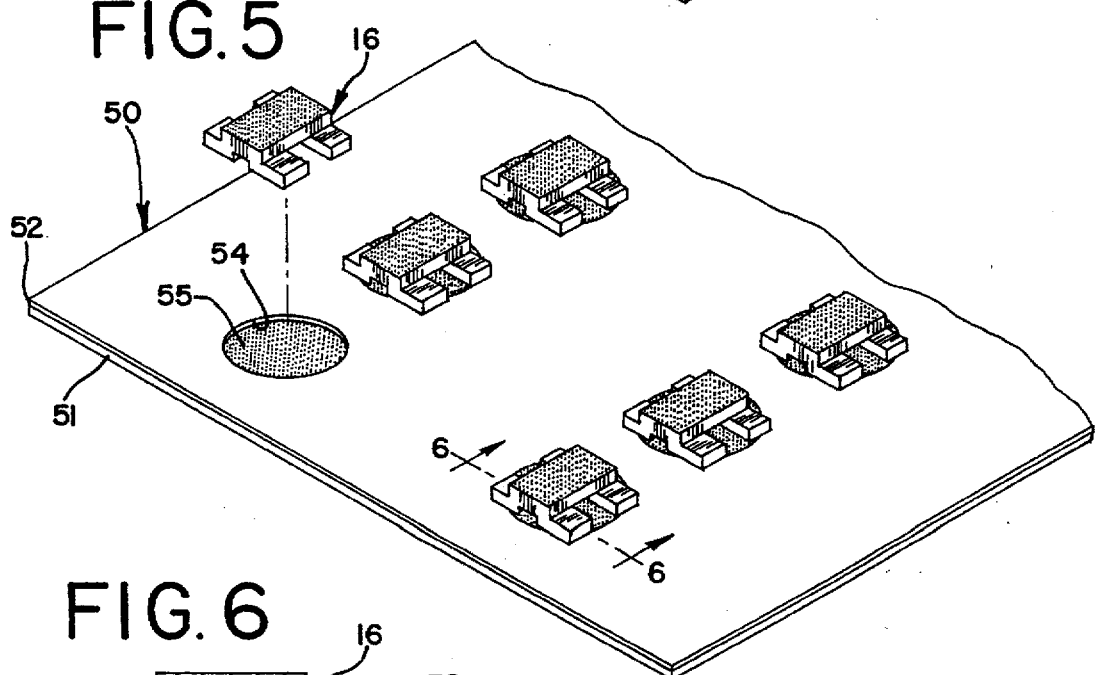
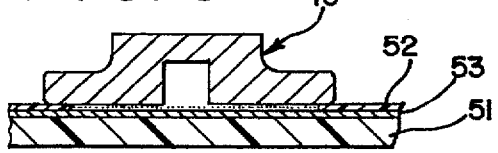

ORTHODONTIC APPLIANCE KIT AND COMPONENTS

This application is based on the provisional application Ser. No. 60/005,442, filed Oct. 12, 1995.

This invention relates in general to an orthodontic appliance kit and components of the kit for use by an orthodontist in preparing bondable orthodontic appliances with a photopolymerizable or light-curable adhesive to be mounted on a patient's teeth, and more particularly to an orthodontic appliance kit including a storage box, bond cards for receiving bondable appliances with adhesive and which can be stored in the storage box, a work box within which a bond card may be loaded with bondable appliances, a bond card cover usable at the chair of an orthodontist for preventing curing during transfer of the brackets to a patient, and a mouth shield to be handled by the patient for delaying the curing.

BACKGROUND OF THE INVENTION

Heretofore, it has been well known to provide bondable appliances with light-curable adhesive, sometimes referred to herein as a photopolymerizable adhesive, to be mounted directly onto the teeth of a patient. Such appliances have sometimes been referred to as prepasted appliances and have been provided directly by the manufacturer in packages from which they are removed for mounting on teeth. Such bondable appliances include brackets, buccal tubes, and other auxiliaries made of metal, ceramic or plastic. Other appliances include lingual attachments, bondable retainers, space maintainers and diastema closures. U.S. Pat. Nos. 4,978,007; 5,172,809 and 5,183,403 relate particularly to packaging of prepasted brackets. It has also been well known to provide photopolymerizable adhesives for bondable appliances such as shown in U.S. Pat. Nos. 3,745,653; 4,204,325; and 5,015,180.

It has also been well known to provide bonding adhesives for orthodontic appliances that are photopolymerizable such that they may easily be cured by the application of a curing light capable of producing actinic radiation. It will be understood that actinic radiation is light energy in the wave length range useful in curing photopolymerizable adhesives. More particularly, actinic rays constitute light rays of short wave length occurring in the violet and ultraviolet parts of the visible spectrum which are capable of producing chemical changes, and in connection with a light-curing adhesive, actinic rays cause curing of the adhesive within short periods of time, such as approximately 10 to 30 seconds, thereby minimizing bonding adhesive curing times, and ultimately the amount of chair time required for a patient receiving appliances.

The packages for prepasted bondable appliances as disclosed in the above patents are formed of materials that will not transmit actinic radiation, thereby maintaining the adhesive on the appliances in an uncured state.

Since these packages in which the prepasted appliances are of a type that are disposable, the cost of the appliances in such packages is substantially more than the cost of buying appliances in bulk quantities. Further, not all orthodontists use the packaged prepasted appliances on the basis they would rather apply the adhesive to the appliances in their own facility to assure its freshness and have the thickness desired. However, the handling of the appliances and the application of adhesive in the orthodontist's office is presently usually completed at the patient's chair and therefore could not be completed in advance before the patient arrives for treatment. The time for applying the adhesive is such that the overall time that the patient must be in the office of an orthodontist for having appliances mounted requires valuable chair time that could be used more efficiently for treating a greater number of patients in a given time period.

SUMMARY OF THE INVENTION

The present invention relates to an orthodontic kit and components in the kit for use in an orthodontist's office to facilitate the handling of bondable appliances where a bondable light-cure, tacky adhesive is applied to the appliances in the office prior to the mounting of the appliances on the teeth of a patient. The kit includes bond cards on which bondable appliances having the light-cure adhesive applied are temporarily mounted in an organized manner by designating the teeth on which the appliances are to be mounted. The kit enables an orthodontic office to purchase brackets or appliances and adhesive in such large quantities that maximum discounts are allowed to reduce costs. Thereafter, the adhesive may be applied to the brackets at a given time prior to the scheduled appointment of a patient. For example, the brackets may be prepared with the bondable adhesive the day before or earlier on the same day prior to the scheduled appointment time of a particular patient. At the time a patient arrives, the bond card with the designated appliances for the patient is retrieved from storage and transferred to the chairside of a patient.

The kit includes a storage box capable of storing a plurality of bond cards with bondable appliances so that bond cards with appliances can be made up in advance for patients and placed in the storage box. The storage box is constructed of material that will shield the appliances against actinic radiation to maintain the adhesive in uncured form. At least a door or cover of the box is preferably transparent so that the contents may be viewed without opening the box, while at the same time being opaque to the wave lengths of light required to cure the adhesive. However, the entire box may be of transparent actinic radiation shielding material. Additionally, other labeling may be provided for the box to facilitate retrieving the desired bond card with appliances for a particular patient.

The kit also includes a work box to be used at the chairside of a patient within which a bond card with bondable appliances such as brackets may be placed and generally shielded against actinic radiation so that the adhesive on the appliances will remain in an uncured state. Appliances are removed from the bond card and mounted in the patient's mouth. It will be appreciated that the adhesive will be of a type that is photopolymerizable or curable by a particular light source, as it is well known that much less time is needed to cure such an adhesive when the appliances are mounted on the teeth of a patient. The work box will have a bottom, possibly sides, and a top all made of an actinic radiation shielding material with one side wall having a large enough opening into which a technician can easily reach with an appropriate tool such as a tweezers and remove an appliance from the bond card for mounting on a tooth. The top wall or panel of the work box will be transparent so that the technician can see the contents of the work box and be able to pick a particular bracket or bondable appliance from the card and know exactly where the appliance is to be mounted in the mouth of a patient. The work box is used preferably prior to a patient's visit for prepasting appliances and placing them in the storage box.

Preferably, a chairside cover made of actinic radiation shielding material is used at the chair of a patient during bonding to shield appliances on a single bond card prior to mounting. Additionally, a mouth shield made of actinic radiation shielding material is preferably used to delay the cure of adhesive once the buckets are positioned on the teeth. This allows the option of mounting all brackets, adjusting their positions and then curing them.

Where the appliances are to be mounted on the bond card with the appliance base facing downwardly toward the card, the card may be made of a material that will be adhesive-releasing so that the appliance may easily be lifted from the bond card to transfer it to the mouth of a patient. While the card may be made of a plastic that is adhesive-releasing, it also may be made of a rigid material, such as cardboard or polystyrene, and have a layer of adhesive-releasing material on the face where the bondable appliances are mounted.

If it is desired to have the bonding face of the appliance facing upwardly, then a standard type bond card that has been used heretofore may be employed which would have a tacky surface on which the face of the appliance may be mounted and which would allow removal without leaving any undesirable adhesive residue on the face of the appliance. Such an acceptable tacky surface would be the adhesive side of a suitable masking tape.

It should also be appreciated that the present invention includes the components by themselves which include the bond cards capable of having the bondable appliances with the bondable base facing downwardly on the card and engaging the card. Further, it should be appreciated that the storage box by itself which is capable of shielding the prepasted appliances from actinic radiation and also having a panel for viewing the contents is unique. Also, the chairside cover and the mouth shield, both of which are made of actinic radiation shielding material, are unique. Finally, the work box, which is sized to make it easy for a technician to reach in and apply prepasted appliances on cards and to remove bondable appliances from a bond card and also to be able to view the contents during the time the removal procedure is being accomplished as well as shielding the appliances on the card against actinic radiation, is unique.

The invention also involves the method of preparing and using bondable orthodontic appliances with photopolymerizable adhesive that includes the application of the adhesive to the bonding bases of the appliances, releasably mounting the appliances on bonding cards having a releasable surface, placing the cards into a storage box that will allow viewing the bonding cards in the box so that the cards for given patients can easily be identified, transferring a bonding card to a work box or chairside cover and then finally removing the appliances one at a time from the card disposed in the work box or cover so that they can be then mounted directly on the teeth of a patient. Further, use of the mouth shield during mounting delays the curing until final adjustments can be made, after which a curing light may be used to finalize curing.

The present invention facilitates the handling of bondable appliances in the office of the orthodontist or dentist where the orthodontist or dentist chooses to apply a light-curable adhesive to the bases of the appliances in advance of the time needed to mount the appliances on the teeth of a patient. The storage box, the chairside cover, the mouth shield, and the work box are reusable as long as they are not damaged, while the bond cards may be reusable or disposable in accordance with the desires of the orthodontic office. Accordingly, the cost of bondable appliances that have been prepasted is substantially reduced by the fact that the work can be done in the office, and substantial time is saved during the time the patient is scheduled to be in the office by having the appliances ready and available for mounting when the patient arrives. This eliminates the need to prepaste each appliance individually at the chairside of the patient, as well as the need to purchase expensive packaged prepasted appliances. Moreover, better control of patient prescriptions can be achieved for better practice efficiency.

BRIEF DESCRIPTION OF THE DRAWINGS

FIG. 4 is a perspective view of a work box according to the present invention and illustrating a bond card with brackets mounted thereon located in the work box;

FIG. 5 is a greatly enlarged modified bond card which is of standard construction and capable of mounting the brackets with the base side up;

FIG. 6 is a greatly enlarged transverse sectional view taken substantially along line 6—6 of FIG. 5;

DESCRIPTION OF THE INVENTION

The orthodontic kit of the present invention would be used by an orthodontist or a dentist practicing orthodontia for the purpose of preparing bondable appliances having light-curable adhesive pre-applied to the bases of the appliances in advance of a scheduled appointment of a patient for which the appliances are to be used for orthodontically treating the patient. While the appliances might include any type of bondable appliances, for the purposes of illustrating the invention the chosen appliance will be brackets for mounting on the teeth of patients, although it should be appreciated that any type of bondable appliance may be used with the kit of the present invention.

The orthodontic kit of the present invention provides the orthodontist with the ability to customize a selection of bondable appliances for a given patient and having those appliances prepasted and ready for mounting on the teeth of the given patient. When the patient makes the scheduled appointment in the office of the orthodontist, the appliances are prepasted or applied with light-curable adhesive on the bases or mounting pads so that they may be first mounted on the teeth of a patient and then treated with a light for curing the adhesive which completes the mounting process.

Where the particular bondable appliances takes the form of a bracket, it will be appreciated that the bracket may be made of steel, ceramic, or plastic, and that the base of the bracket may take whatever form is desired which sometimes even includes the use of a mounting pad attached to the bracket.

Figure 2:
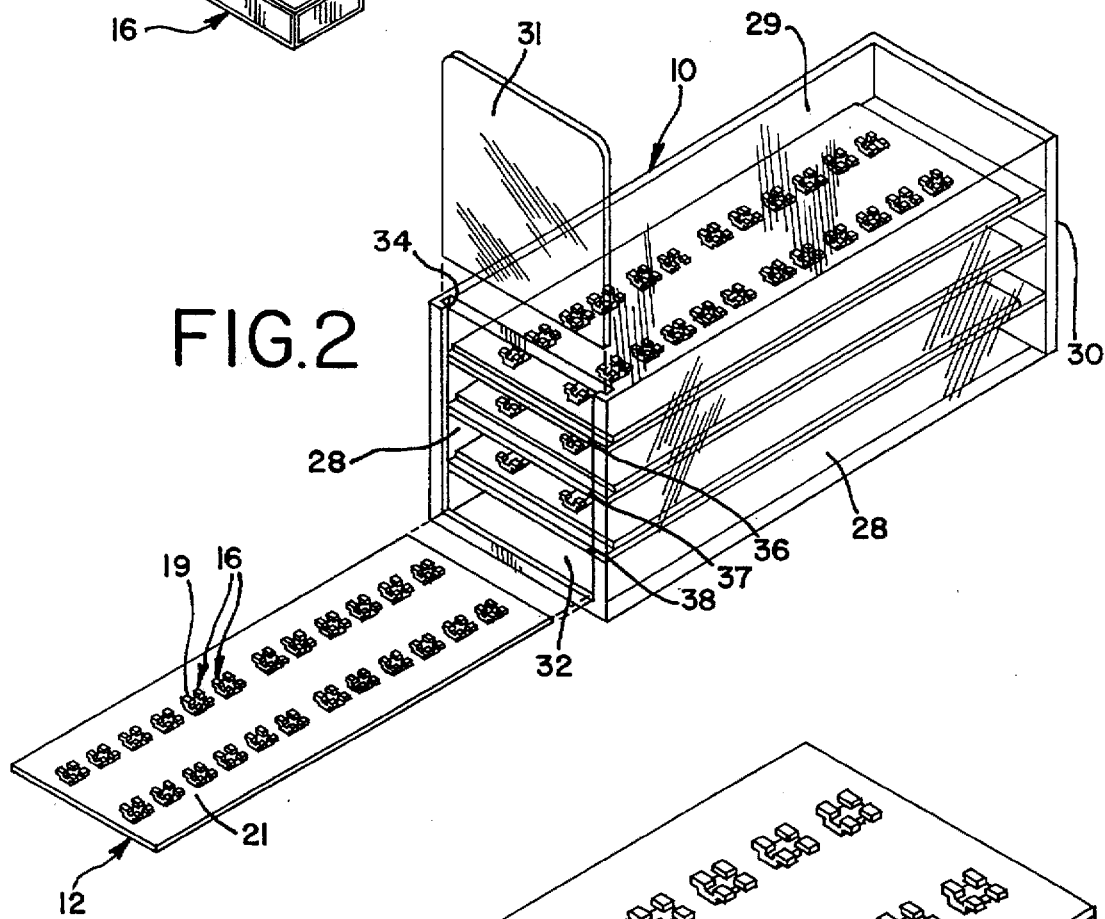
FIG. 2 is perspective and somewhat exploded view of a storage box according to the invention which is capable of storing a plurality of bond cards with brackets mounted thereon in an enclosure that shields actinic radiation but also is transparent so that the contents can be viewed.

The kit of the present invention includes a storage box generally identified by the numeral 10, a plurality of bond cards of a suitable choice, one form of which is generally designated by the numeral 12 in FIG. 2, and a work box, generally designated by the numeral 14, as seen in FIG. 4 for receiving bond cards with the brackets from a storage location, and transferring the cards to the chair of a patient for mounting on the teeth.

It will be appreciated that the bondable appliances are first prepared by applying a photopolymerizable adhesive, or sometimes called a light-curable, tacky adhesive, to the bases of the brackets, after which the brackets are then mounted on a bond card that may also include indicia as to which teeth on which the brackets are to be mounted. The bond cards with the brackets are then placed in the storage box 10 for storage until they are needed for the patient at a scheduled appointment, after which a bond card for a particular patient may be transferred to the work box 14 that would be positioned at the chairside of a patient so that the brackets may be lifted from the bond card one at a time and applied directly to the teeth of a patient. The work box would also be usable during the process of prepasting a set of brackets. Both the storage box and the work box will be of materials that will shield the bondable appliances from actinic radiation that would cure the adhesive and further the storage box and the work box would have transparent walls or panels so that the interior can be viewed prior to either removing a bond card with appliances from the storage box or removing appliances from a bond card in the work box and mounting them on teeth. Thus, a transparent actinic radiation shielding material, such as amber or orange plastic, would be used to construct the storage box and work box. A suitable plastic may be #2422 amber Plexiglas plastic made by Rohm & Haas. "Plexiglas" is a trademark owned by Rohm and Haas.

Figure 1:
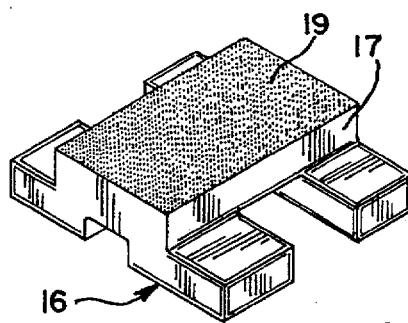
FIG. 1 is a perspective view of an orthodontic bracket with the base portion facing upwardly and illustrating the base as having a light-cure adhesive applied thereto.
Figure 3:
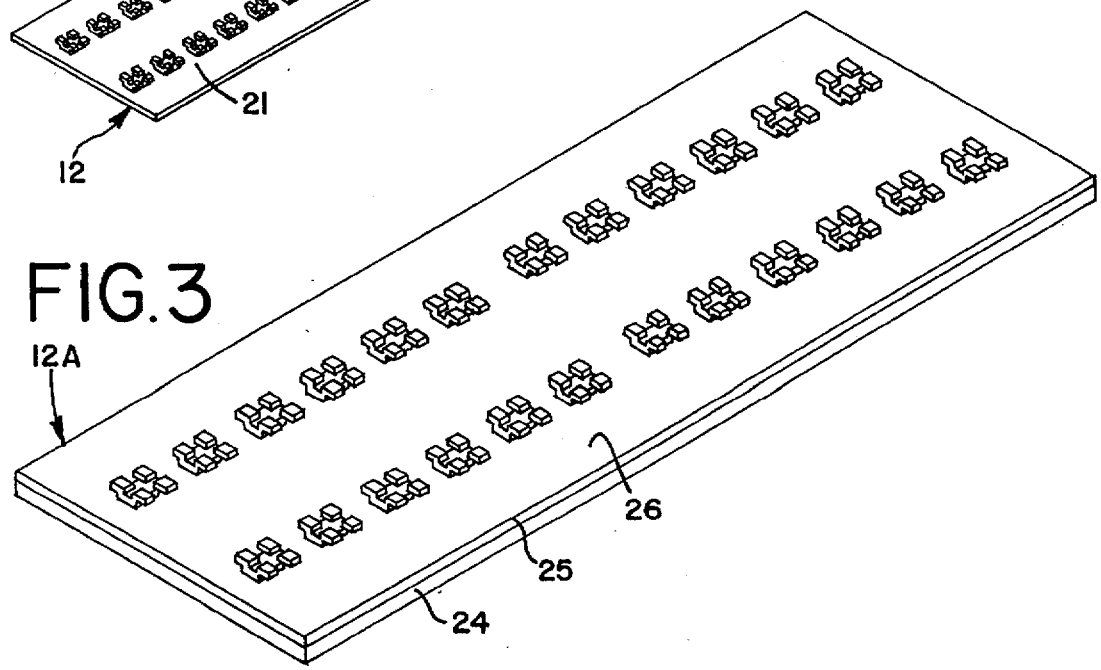
FIG. 3 is a perspective view of a modified bond card which shows the brackets being mounted on a layer of adhesive-releasing material laminated to a rigid substrate.

As seen in FIG. 1, an orthodontic bracket 16 is illustrated which includes a base 17 on which light-curable adhesive 18 has been applied. The bracket has a base side on which the adhesive is mounted and a front face that is illustrated in the brackets of FIG. 2 where the front side is designated by the numeral 19 and as seen in FIGS. 2 and 3. The front side or the profile side of the bracket is facing upwardly, while the base side or tacky adhesive side is facing down and in engagement with the bond card. This is one way of mounting the brackets on the bond card, while another way is illustrated in FIG. 5 where the base side of the bracket is facing upwardly, as will be more clearly explained below.

The bond card 12 in FIG. 2 is one version of a bond card and which is made of a sheet of plastic material, such as a high-density polyethylene, that would have an adhesive-releasing surface 21 on which the brackets would be mounted with the prepasted bases. Further, the card may be made of any non-adhesive release-coating material. Further, the card would have a rigidity such that it can be easily handled and would be self-supporting if only supported on the opposite edges.

It will be appreciated that the adhesive herein used, when applied to the base of a bracket, is tacky but is in an uncured state. Further, it will be appreciated that adhesive can be purchased in bulk quantities as the brackets can be purchased in bulk quantities and prepasted brackets may be prepared in accordance with the desire of the orthodontist for a particular given patient. Thus, it is important that the bracket, when mounted face up as shown in the embodiment of FIG. 2, where the adhesive side of the bracket engages the bond card, that the bond card have a surface that is adhesive-releasing so that the brackets may be easily removed from the bond card with the adhesive still intact on the base of the bracket.

Another form of bond card is illustrated in FIG. 3 wherein the bond card is generally designated by the numeral 12A and includes a base 24 of rigid material, such as cardboard or polystyrene, having laminated to the upper side thereof a layer of adhesive-releasing material 25, such as a Mylar film. "Mylar" is a trademark of DuPont for a film of polymer material which would be adhesive-releasing like the high-density polyethylene substrate of the bond card 12. More particularly, the bond card 12A would include a relatively rigid base substrate 24 and adhesive-releasable substrate 25 suitably laminated or bonded to the base layer 24 so that prepasted brackets may be mounted on the releasable surface 26 of the layer 25 and held in place by the tacky adhesive, whereby the brackets may be easily removed with the tacky adhesive layer on the bracket base intact so as to provide a properly adhesively coated base of the bracket when mounting the bracket on a tooth of a patient. Alternately, the base layer or substrate 24 may be suitably coated with an adhesive-releasing material, such as a silicone, polyethylene, or fluoropolymer such as a polytetrafluoroethylene or the like.

The format of the cards shown are illustrative only, as the format may take any desirable arrangement. For example, the spots for receiving brackets may be arranged in two rows adjacent one of the edges, thereby leaving adequate room for the application of other information.

The storage box 10 may take many forms which would include an inner compartment for receiving one or a plurality of bond cards with brackets or appliances mounted thereon and which would be formed of a material that shields actinic radiation so as to the prevent the adhesive from curing during the time the prepasted appliances are stored within the box. Further, at least one panel of the box would be transparent although actinic radiation shielding, so that the contents of the box may be viewed by a technician. Preferably, the box is made of suitably colored plastic panels, which would be transparent while shielding against actinic radiation. The box 10 includes opposed side walls 28, a top wall 29, an end wall 30, and an open end opposite the end wall 30 which would receive a cover or closing panel 31. Opposite the top wall or panel 29 is a bottom wall 32. As seen in FIG. 2, the cover panel 31 is slidably received in vertical slots 34 formed in the side walls 28, so that substantially no actinic radiation can pass around the panel. Within the storage box a plurality of shelves are provided so that a bond card may be stored on each of the shelves as well as the bottom wall 32. Any number of shelves may be provided. In this case shelves 36, 37 and 38 are arranged in substantially equally spaced apart relationship so that a total of four bond cards may be stored within the box, one on each shelf and one on the bottom. As above mentioned, the side walls, top, bottom, end wall, and cover or door 31 are made of actinic radiation shielding material. However, it may be appreciated that only the cover 31 and/or the top wall 29 need to be made of transparent actinic shielding material so that the interior contents of the storage box can be viewed.

At least one panel of the box should be transparent so that a person may easily determine the contents of the storage box. Additionally, it should be appreciated that labels may be provided on the door for purposes of identifying the stored bond cards with respect to the patients for which they have been prepared.

It will be further appreciated that the storage box need not be located chairside but may be remotely located from the chairs in which the patients would be treated. Further, it may be appreciated that the storage box may take other configurations than in the form of the rectangular box illustrated in FIG. 2. In any event, the storage box would allow access to the compartment within the box, be constructed to store one or a plurality of bond cards and have all walls and the door made of actinic shielding material and at least one panel made of transparent actinic radiation shielding material so that the interior contents can be viewed to facilitate identification of the contents.

Once the bond cards are prepared and stored in the storage box, they are ready for use with a patient, and they may be removed from the box one at a time or however needed in order to be ready for use in mounting brackets on the teeth of a patient. In order to facilitate the handling of the bond cards at the chairside, the work box 14 may be used, which allows the temporary storage of a card during a time brackets are being removed from the card. Further, the work box would be used during the prepasting of the brackets, where a bond card would be placed in the work box and as paste is applied to a bracket, the prepasted bracket would be inserted in the box and applied to the card. As seen in FIG. 4, a single bond card 12 is arranged within the work box 14. This work box is comprised of a bottom wall 40, a top wall 41, opposed end walls 42, and a back wall 43. The entire side of the work box opposite the back wall 43 is open at 44 to allow easy access within the box for removal of the brackets one at a time from the bond card 12 or for mounting prepasted brackets one at a time onto a bond card. The box is again made of actinic shielding material and at least the top panel or wall 41 is transparent so that the interior of the box may be easily viewed. Further, the distance between the top wall and bottom wall and the side walls is such as to allow easy access with a person's hand so that they may, by use of a tool such as a tweezers, remove one bracket at a time from the bond card or mount one bracket at a time onto a card. For example, a person may hold the card with one hand in place on the bottom wall, while grasping a bracket with a tweezers with the other hand, thereby leaving the remaining brackets on the bond card until they are ready to be immediately mounted onto the teeth of a patient, or a person may hold the card while placing a prepasted bracket onto the card. Thus, the size of the opening 44 is such as to provide easy access by a person who is in the process of mounting brackets on the teeth of a patient. Further, it is noted that the top wall 41 of the box extends forwardly beyond the bottom wall 44 to provide additional protection against actinic radiation from impinging on the adhesive of the brackets on the bond card. While the work box may be of any suitable dimension or shape, one satisfactory shape would be rectangular, as shown, wherein the width of the top wall and the bottom wall would be about 15½ inches, the depth of the top wall would be about 12¼ inches, and the depth of the bottom wall would be about 10½ inches. Further, the vertical distance within the interior of the box between the top and bottom walls may be approximately six inches. It will be appreciated that the walls of the box are made of suitable rigid material so as to provide a structurally sound box.

Furthermore, the bond cards may be made of any suitable size, it will be appreciated that they may be on the order of 2½ inches wide and 6 inches long. It may also be appreciated that the size of the storage box 10 therefore would be such as to easily accommodate the bond cards within the box. For example, the width and height of the box may be about 3 inches, while the length and depth of the box may be about 7 inches.

In FIGS. 5 and 6, the heretofore well known bond card, generally designated by the numeral 50, is illustrated, which includes a rigid base material 51 having laminated thereto a relatively thin film of polyethylene or other suitable type of material 52. Between the top sheet 52 and bottom base 51 a suitable adhesive-backed tape 53 may be provided, such as masking tape, with the tacky surface facing upwardly. A plurality of cutouts 64 are provided along the top layer 52 to expose the tacky adhesive surface 55 of the masking tape 53. This provides an area where the front face side of a bracket may be adhesively mounted on the bond card. It is well known that masking tape adhesive is tacky and would allow removal of a bracket mounted thereon while avoiding any undesirable adhesive residue to be transferred to the bracket face. Thus, the plurality of openings in the upper layer would provide sites for mounting the brackets 16 as illustrated in FIG. 5. Therefore, if it is desired to have the base side of the bracket with adhesive thereon facing upwardly, the bond card 50 would be employed for mounting the brackets. The use of these bond cards in the work box would be the same as when the adhesive side of the bracket is facing downwardly. It may therefore be appreciated that any type of bond card may be employed with the orthodontic kit of the present invention.

Figure 7:
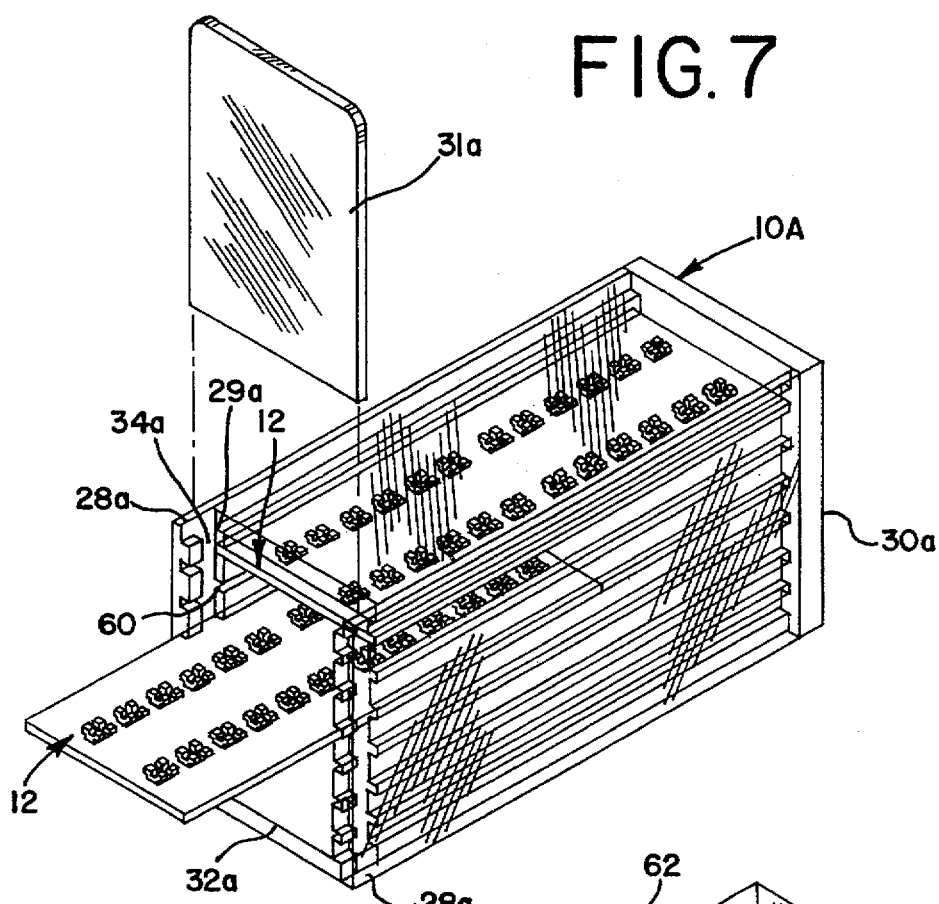
FIG. 7 is a perspective view of a modified storage box according to the present invention.

A modified storage box according to the invention is illustrated in FIG. 7 and generally indicated by the numeral 10A. This storage box serves essentially the same purpose as the storage box 10 of FIG. 2 but is sized and provided with slideways for receiving the bond cards. Thus, this storage box does not include shelves for bonding cards as in the embodiment in FIG. 2.

The storage box 10A includes opposed side walls 28a, a top wall 29a, an end wall 30a, a closing panel or door 31a, and a bottom wall 32a. At least the side, top, and end walls, together with the door, are preferably made of a transparent actinic radiation shielding material such as amber Plexiglas plastic so that bond cards with prepasted brackets or appliances can be viewed when the storage box is closed while guarding against the curing of the adhesive. Vertical slots 34a are provided in opposed relation at the inlet ends of the wide walls 28a for purposes of slidably receiving the door 31a. Preferably, the fit between the door and the slots is as close as possible to preclude light from entering the box that would cause the adhesive to cure. When the door 31a is in closed position, it rests on the bottom wall 32a and completely covers the front opening of the storage box to shield the interior compartment against light energy that would cause curing of the adhesive on the appliances.

Rather than utilizing shelves for supporting bond cards, as illustrated in embodiment 10 of FIG. 2, the side walls of the box include slideways 60 for slidably receiving the opposed edges of the bond cards and supporting the bond cards at a particular level within the box. While six such sets of slideways are illustrated, it would be appreciated that any number may be provided in a storage box to handle any number of bond cards. A bond card 12 is shown in the uppermost set of slideways within the box, as it would be located so that the door 31a could be placed in position over the end of the opening of the box. A second bond card 12 is shown in the third set of slideways from the top in a position partially within and partially on the outside of the box to illustrate how the bond cards are inserted into the box. It will be appreciated that the dimensions of the box are such as to accept bond cards of a particular given size that can be received by the slideways and supported in a designated position within the box. Accordingly, the storage box may be used to store prepasted brackets or appliances on bond cards until they are to be used for mounting onto a patient's teeth.

Figure 8:
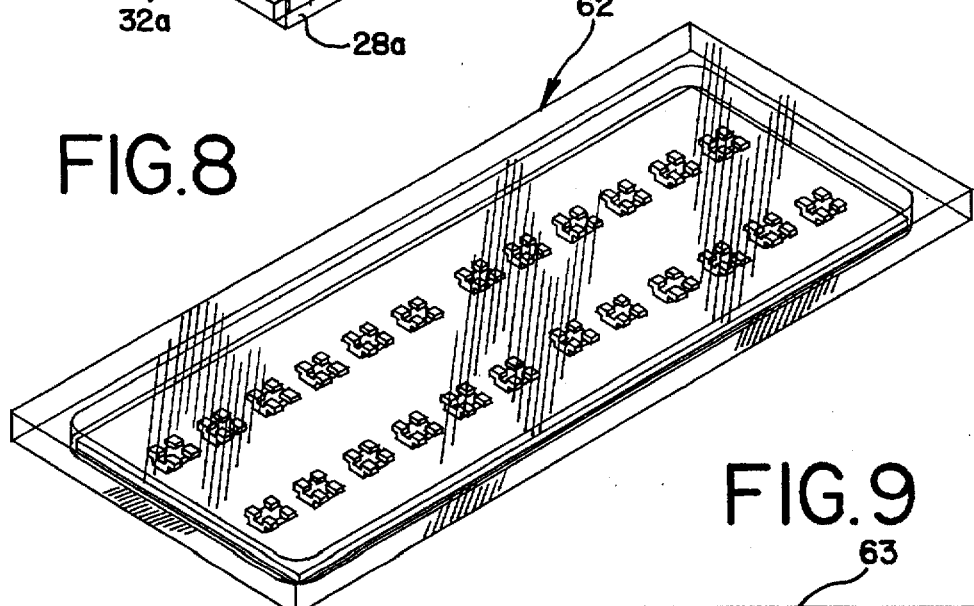
FIG. 8 is a perspective view of a chairside cover according to the present invention.
Figure 9:
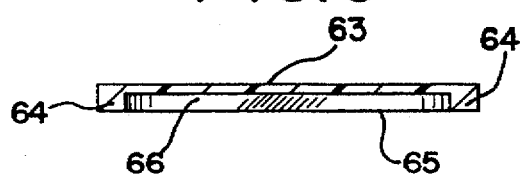
FIG. 9 is a transverse sectional view taken through the chairside cover of FIG. 8.
Figure 10:
FIG. 10 is a longitudinal sectional view taken through the chairside cover of FIG. 8.

While it is possible to use the work box 14 at the chairside for handling of a bond card with prepasted brackets, it would be preferable to use the work box only in the laboratory during the process of mounting prepasted brackets on a bond card. More preferably, a chairside cover 62 would be used for handling the bond cards with prepasted brackets at the chairside of a patient. This chairside cover is much more compact and is sized to fit over a single bond card waiting to be used for mounting of brackets on the teeth of a patient. As particularly seen in FIGS. 8 to 10, bond card cover 62 is rectangularly formed and includes a top wall 63, opposed side walls 64, and opposed end walls 65 coacting to define with a table or counter on which it may be positioned, a compartment 66 within which a bond card may be received, as illustrated in FIG. 8. During the mounting of brackets on a patient's teeth, the bond card cover may be lifted while the clinician separates a bracket from the bond card for mounting on a tooth, after which the bond card may be lowered to the table or counter to protect the adhesive on the remaining brackets from being exposed to light that would tend to start the curing of the adhesive. Thereafter, the bond card cover may be lifted for retrieval of additional brackets to be mounted on teeth. Thus, the chairside bond card cover will serve to delay the curing of the adhesive on the brackets during the overall mounting procedure.

The entire bond card cover may be made of transparent actinic radiation shielding material, as shown, or at least the top wall is made of this material so that the bond card can be viewed by the clinician.

Figure 11:
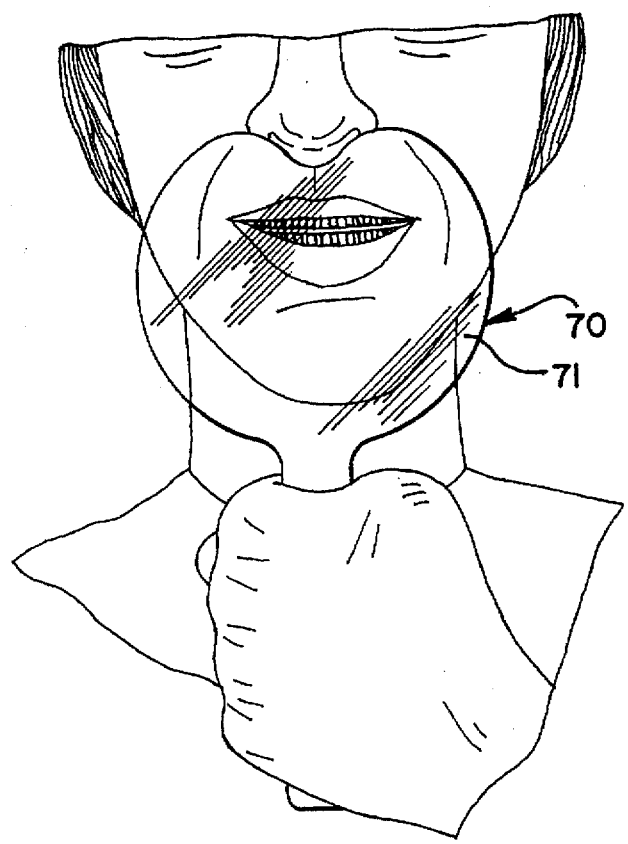
FIG. 11 is a fragmentary frontal view of a patient holding a mouth shield of actinic radiation shielding material during the process of mounting prepasted brackets in order to delay curing of adhesive on the brackets.
Figure 12:
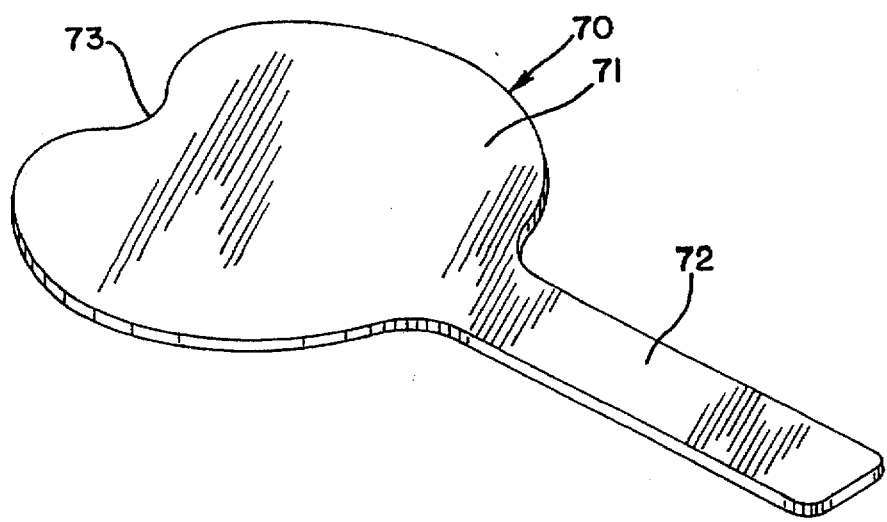
FIG. 12 is a perspective view of the mouth shield of FIG. 11.

In order to additionally protect against curing of adhesive on the brackets during the mounting procedure, a mouth mask or shield 70 is provided for handling by the patient to cover the mouth prior to the final positioning of the brackets on the teeth and the administering of a curing light to cure the adhesive on the brackets, while at the same time to allow the clinician to view the positioning of the brackets in order to make a determination as to whether adjustment needs to be made prior to final curing. This mouth shield is also made of transparent actinic radiation shielding material such as amber Plexiglas plastic and is in the form of a fan having a somewhat rounded shield member 71 connected to a handle 72. The shield member 71 is sized so that it will adequately cover the mouth of a patient, as illustrated in FIG. 11, and also includes at its upper end a cutout 73 shaped to somewhat fit under the nose of a patient, as shown in FIG. 11. Thus, a patient will be provided with the mouth shield whereby the handle is gripped by the hand of a patient and positioned over the mouth during the times when the clinician is engaged in the mounting procedure and not needing to have access to the mouth so that the cure of the adhesive on the brackets may be delayed if desired once the brackets are initially positioned. The mouth shield therefore will allow the option of mounting all brackets, adjusting them, and then curing the brackets or doing so with respect to only some of the brackets during the overall mounting procedure.

From the foregoing it can readily be appreciated that the orthodontic kit may include a work box, a storage box, bond cards for prepasted appliances, a bond card cover, and a mouth shield. Further, the storage box, bond card cover and work box would shield the adhesive on the appliances from substantially all actinic radiation to maintain the adhesive in an uncured state. Similarly, the mouth shield would shield against actinic radiation. It may also include, of course, a light-cure adhesive and/or a curing light. However, the orthodontist's office would normally buy an adequate supply of light-curable adhesive and a supply of bond cards which may or may not be disposable. The office would also purchase brackets and adhesive in bulk quantities to reduce cost by obtaining the best possible discount. As above explained, in operation, the brackets would be prepasted, that is, they would have light-cure adhesive applied to their bases, and then be mounted on the bond cards, stored in the storage box, and then ultimately transferred one at a time to a work box or a bond card cover where the brackets could be removed from the bond cards and mounted on the teeth of a patient after the teeth are suitably prepared for bonding. Obviously, once the brackets are properly positioned on the teeth of a patient, and any excess adhesive is removed, the adhesive on the bracket base could be light-cured in the usual fashion with a standard well known curing light, such as the lights sold by American Orthodontics Corporation of Sheboygan, Wis. Further, a suitable adhesive could be the Spectrum adhesive marketed by the same company. "Spectrum" is a trademark owned by American Orthodontics Corporation. During the mounting procedure, the mouth shield may be used to delay curing.

It will be understood that modifications and variations may be effected without departing from the scope of the novel concepts of the present invention, but it is understood that this application is to be limited only by the scope of the appended claims.

The invention is hereby claimed as follows:

1. An orthodontic kit for preparing prepasted brackets including bases having a paste curable by exposure to actinic radiation, and facilitating the mounting of the brackets in the mouth of a patient, said kit including:

a substantially planar bond card on which prepasted brackets may be mounted in a predetermined manner for use to transfer the brackets to the patient, a storage box for storing a bond card with prepasted brackets, said box being made of actinic radiation shielding material at least some of which is transparent so the contents can be viewed, a work box of transparent actinic radiation shielding material for receiving a bond card and being of a size to provide easy access to facilitate the application of pasted brackets to the card while protecting the pasted brackets from exposure to actinic radiation, a bond card cover for use at chairside for covering a bond card and being of transparent actinic radiation shielding material to prevent actinic radiation from reaching the paste on the brackets while allowing visual inspection thereof, and a mouth shield of transparent actinic radiation shielding material for use by the patient over the mouth to delay curing of adhesive on brackets mounted in the mouth.

2. A bond card for removably receiving a plurality of orthodontic appliances having bonding bases with a tacky photopolymerizable adhesive applied thereto, said bond card including a substantially planar and rigid substrate having a surface for releasably receiving the tacky adhesive base of the appliances, the rigidity of the substrate being such as to be self-supporting, whereby the card can easily be handled and the appliances can be removed from the card without disturbing the adhesive.

3. The bond card of claim 2, wherein the substrate is formed of a tacky adhesive-releasing high-density polyethylene.

4. The bond card of claim 2, wherein the substrate is formed of a cardboard base having a tacky adhesive-releasing surface on which the appliances are mounted.

5. The bond card of claim 2, wherein the substrate is formed of polystyrene having a tacky adhesive-releasing surface on which the appliances are mounted.

6. The bond card of claim 2, wherein the entire surface of the card is of tacky adhesive releasing material.

7. The bond card of claim 2, wherein the surface includes a plurality of sites of tacky adhesive releasing material on which the appliances may be mounted.

8. The bond card of claim 2, wherein the rigidity of the substrate is such that the card can be easily handled and be self-supporting if only supported at the opposite edges.

9. A storage box for storing a substantially planar bond card having a plurality of orthodontic appliances mounted thereon, bonding bases on the appliances having photopolymerizable adhesive applied thereto, said adhesive being curable by exposure to actinic radiation, said storage box including a box defining a storage compartment having means for receiving a bond card having appliances removably mounted thereon, said box including an opening through which a bond card may pass and a closure for closing the opening, said box and closure formed of a material capable of shielding the compartment of said box from actinic radiation, and at least the box or closure being transparent to allow viewing of the storage compartment.

10. The storage box of claim 9, wherein the box includes a bottom wall, side walls extending upward from the bottom wall, a top wall between the side walls, an end wall connecting the bottom, sides and top walls, all defining said compartment having said opening that receives the closure, said compartment sized to receive a bond card, and said side, top and end walls being of transparent actinic radiation shielding material.

11. The storage box of claim 9, wherein said means includes a plurality of shelves for receiving a plurality of bond cards in spaced apart relation.

12. The storage box of claim 9, wherein said means includes a plurality of slideways for slidably receiving and supporting a plurality of bond cards in spaced apart relation.

13. A work box for receiving a substantially planar bond card having orthodontic appliances removably mounted thereon with bonding bases on the appliances having photopolymerizable adhesive applied thereto, said adhesive being tacky and curable by being subjected to actinic radiation, said work box being formed of an actinic radiation shielding material and having a bottom wall on which a bond card may be received, a top wall supported from and overlying the bottom wall, and at least one open side through which appliances may be placed on or removed from the bond card, said bottom and top walls being spaced apart for defining an interior space sized to allow easy access by a hand of a worker for placing or removing appliances on the bond card while protecting the adhesive from actinic radiation, and at least the top wall being transparent to allow viewing of the interior space.

14. The work box of claim 13, which further includes side walls and an end wall of transparent actinic radiation shielding material.

15. The method of preparing and using orthodontic appliances bondable to teeth and having bases with photopolymerizable adhesive applied thereto, said method comprising the application of a photopolymerizable adhesive to bonding bases of orthodontic appliances, said adhesive being curable by being exposed to actinic radiation, releasably mounting the appliances on substantially planar bonding cards having a releasable surface, placing the cards in spaced apart relation into a storage box formed of actinic radiation shielding material with at least a portion of said box being transparent to allow viewing the bonding cards in the box, transferring a bonding card to a work box defining an interior and being formed of actinic radiation shielding material and having an access opening for removing appliances from the card and a transparent portion for viewing the interior of the box, and removing appliances from the card disposed in the work box for mounting onto teeth.

16. The method of claim 15, which further includes the step of providing the patient with a mouth shield made of transparent actinic radiation shielding material for use by the patient to delay curing of adhesive on brackets placed on teeth and allow the option of mounting all brackets, adjusting them, and then curing the adhesive of said brackets with a light source.

17. The method of preparing and using orthodontic appliances bondable to teeth and having bases with photopolymerizable adhesive applied thereto, said method comprising the application of a photopolymerizable adhesive to bonding bases of orthodontic appliances, said adhesive being curable by being exposed to actinic radiation, releasably mounting the adhesive bases of the appliances on substantially planar bonding cards having a releasable surface, placing the cards into a storage box formed of actinic radiation shielding material with at least a portion of the box being transparent to allow viewing the bonding cards in the box, transferring a bonding card with appliances to a bond card cover disposed adjacent a patient, and removing appliances from the card disposed in the bond card cover for mounting onto teeth of the patent.

18. An orthodontic kit for preparing and using orthodontic appliances bondable to teeth, wherein the appliances include bonding bases having photopolymerizable adhesive curable by actinic radiation applied thereto, said kit including substantially planar bond cards on which the appliances are mounted, a storage box for storing a plurality of bond cards with appliances, and a work box for receiving a bond card with appliances wherein the appliances may be placed on or removed from the card and mounted on teeth, said bond cards having a surface on which the appliances are releasably mounted, said storage box including a box defining a compartment and an openable cover or panel closing the box and formed of a material capable of shielding the interior from actinic radiation and at least the cover or panel being transparent to allow viewing the compartment, said storage box being compact for storage purposes, and said work box including a bottom and a top wall supported over the bottom shielding the compartment from actinic radiation and at least the top wall being transparent to allow viewing the compartment, and said work box having at least one side open and sized to allow a worker to reach into the compartment and place on or remove appliances from a bond card disposed therein while protecting the adhesive from actinic radiation.

19. The kit of claim 18, which further includes a chairside bond card cover for receiving and covering a bond card and being at least partially made of transparent actinic radiation material so that a bond card received thereby can be viewed.

20. A bond card cover for covering a substantially planar bond card on an actinic radiation shielding supporting surface, wherein the card includes prepasted orthodontic appliances removably mounted thereon, said prepasted appliances including bases having a light-curable tacky adhesive thereon curable by exposure to actinic radiation, said bond card having a tacky adhesive releasing surface for releasably receiving the tacky adhesive on the appliance bases, said cover being substantially of transparent actinic radiation shielding material and including a space accommodating a bond card with appliances thereon and a periphery for contacting said supporting surface to substantially block the passage of actinic radiation into said space.

21. In combination with an orthodontic appliance having a bonding base with a tacky photopolymerizable adhesive applied thereto, a substantially planar bond card including a relatively rigid substrate having a surface for releasably receiving the tacky adhesive base of the appliance, the rigidity of the substrate being such that it is self-supporting when supported at opposite edges, whereby an appliance may be removed from the bond card without disturbing the adhesive.

* * * * *

UNITED STATES PATENT AND TRADEMARK OFFICE
CERTIFICATE OF CORRECTION

PATENT NO. : 5,697,780
DATED      : December 16, 1997
INVENTOR(S): Lee H. Tuneberg and John E. Viglietti It is certified that error appears in the above-indentified patent and that said Letters Patent is hereby corrected as shown below:

```
Col. 6, line 42, delete the first occurrence of "the"
Col. 8, line 14, change "64" to --54--
Col. 12, line 43, change "patent" to --patient--
```

Signed and Sealed this

Fourteenth Day of April, 1998

Attest:

BRUCE LEHMAN

Attesting Officer

Commissioner of Patents and Trademarks